United States Patent [19]

Theodoridis

[11] Patent Number: 4,894,084
[45] Date of Patent: Jan. 16, 1990

[54] SUBSTITUTED QUINOLINONYL AND DIHYDROQUINOLINONYL TRIAZOLINONE HERBICIDES

[75] Inventor: George Theodoridis, Princeton, N.J.

[73] Assignee: FMC Corporation, Philadelphia, Pa.

[21] Appl. No.: 138,975

[22] Filed: Dec. 29, 1987

[51] Int. Cl.$^4$ .................. A01N 43/64; C07D 401/04
[52] U.S. Cl. ........................ 71/92; 546/155; 546/156; 546/157; 546/158
[58] Field of Search .............. 546/155, 156, 157, 158, 546/153; 514/312, 314; 71/92

[56] References Cited

U.S. PATENT DOCUMENTS 4,619,687 10/1986 Haga et al. ......................... 71/92
4,761,174 8/1988 Chang et al. ....................... 71/92

FOREIGN PATENT DOCUMENTS 0176101 4/1986 European Pat. Off. .
61-165383 7/1986 Japan .

OTHER PUBLICATIONS

Derwent Abstracts, Accession No. 86-235782, abstract of JP61-165383 (above) Sumitomo Chem. (1985).

Primary Examiner—Mukund J. Shah
Assistant Examiner—Andrew G. Rozycki
Attorney, Agent, or Firm—Robert M. Kennedy; H. Robinson Ertelt; Abner Sheffer

[57] ABSTRACT

Quinolinone compounds of the formula

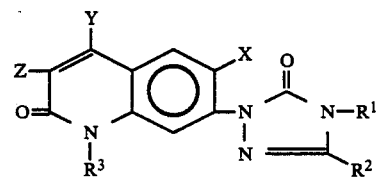

in which $R^3$ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy; X is H, halogen, alkyl, or haloalkyl; Y is H, halogen, alkyl, haloalkyl, alkoxycarbonyl, cyano, or nitro; Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro; $R^1$ is alkyl, alkenyl, alkynyl, haloalkyl, alkoxyalkyl, or haloalkoxyalkyl; and $R^2$ is alkyl, haloalkyl, alkoxy, haloalkoxy, alkylthio, alkylsulfinyl, alkylsulfonyl, or halogen; and the corresponding 3,4-dihydroquinolinone compounds as herbicides.

28 Claims, No Drawings

SUBSTITUTED QUINOLINONYL AND DIHYDROQUINOLINONYL TRIAZOLINONE HERBICIDES

The invention described in this application pertains to weed control in agriculture, horticulture, and other fields where there is a desire to control unwanted plant growth. More specifically, the present application describes certain herbicidal aryl triazolinones, compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species. The present invention is particularly useful in agriculture as a number of the compounds described herein show a selectivity favorable to certain crops (e.g. cotton) at application levels which inhibit the growth of or destroy a variety of weeds.

One aspect of this invention relates to triazolinones of the following formula I and their use as herbicides:

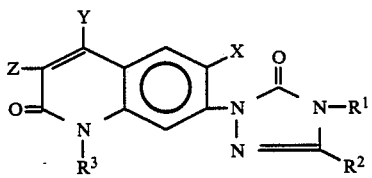

Formula I in which $R^3$ is:
H;
alkyl, e.g. methyl, ethyl, propyl, or isopropyl;
alkenyl, e.g. allyl or methallyl;
alkynyl, e.g. propynyl or methylpropynyl;
haloalkyl, e.g. 3-chloropropyl, 2-fluoroethyl, or 3-fluoropropyl;
haloalkenyl, e.g. 3,3-dichloro-2-propenyl;
alkoxyalkyl, e.g. methoxymethyl or ethoxymethyl;
alkoxyalkoxyalkyl, e.g. ethoxymethoxymethyl;
cycloalkyl, e.g. cyclopropylmethyl;
alkylthioalkyl, e.g. methylthiomethyl;
aralkyl, e.g. benzyl;
cyanoalkyl, e.g. cyanomethyl;
alkoxycarbonylalkyl e.g. methoxycarbonylmethyl;
hydroxy; or alkoxy, e.g. methoxy or ethoxy.

X is H, halogen (such as F, Cl or Br), alkyl (e.g. methyl), or haloalkyl (e.g. difluoromethyl);

Y is H, halogen (e.g. F, Cl or Br), alkyl (e.g. methyl), haloalkyl (e.g. difluoromethyl), alkoxycarbonyl (e.g. ethoxycarbonyl), cyano, or nitro.

Z is H, halogen (e.g. F, Cl or Br), alkyl (e.g. methyl), haloalkyl (e.g. difluoromethyl), alkoxy (e.g. methoxy), alkenyl (e.g. allyl), alkynyl (e.g. propynyl), haloalkoxy (e.g. difluoromethoxy), alkylthio (e.g. methylthio), alkylsulfinyl (e.g. methylsulfinyl), alkylsulfonyl (e.g. methylsulfonyl), alkoxycarbonyl (e.g. ethoxycarbonyl), cyano, or nitro.

$R^1$ is alkyl (e.g. methyl), alkenyl (e.g. allyl), alkynyl (e.g. propynyl), haloalkyl (e.g. difluoromethyl, 2-fluoroethyl, or 3-fluoropropyl), alkoxyalkyl (e.g. methoxymethyl), or haloalkoxyalkyl (e.g. difluoromethoxymethyl).

$R^2$ is alkyl (e.g. methyl), haloalkyl (e.g. difluoromethyl), alkoxy, (e.g. methoxy), haloalkoxy (e.g. difluoromethoxy), alkylthio (e.g. methylthio), alkylsulfinyl (e.g. methylsulfinyl), alkylsulfonyl (e.g. methylsulfonyl), or halogen (e.g. F, Cl or Br).

In each aspect of the invention it is often preferable that any alkyl, alkenyl, alkynyl or alkylene group or moiety (such as the hydrocarbon moiety of an alkoxy or haloalkoxy group) have up to 6 carbon atoms, e.g. 1 to 4 carbon atoms and any cycloalkyl have 3 to 7 ring carbon atoms.

The compounds of this invention may be prepared by the use of steps generally described in the literature or in the following Example or by methods analogous or similar thereto and within the skill of the art. In the Example below, a compound of the formula

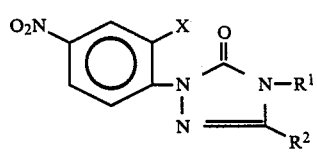

Formula II was reduced to convert the nitro group to an amino group, after which the resulting amino compound was reacted with a compound of the formula YHC=C(-Z)—C(O)—$X^3$ where $X^3$ is, for instance, a lower alkoxy group. This reaction was effected, according to a modification of the known Meerwein reaction involving formation of a diazonium halide and its reaction with an olefin in the presence of a copper halide, to form a compound of the formula

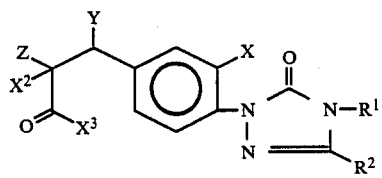

Formula III where $X^2$ is halogen (such as Cl or Br). The resulting compound was then nitrated to form a compound of the formula

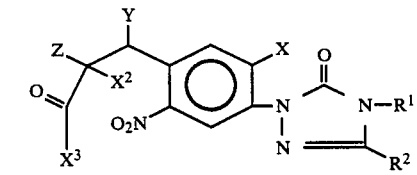

Formula IV

Then, by reaction involving treatment with iron in an acidified solvent, (e.g. at an elevated temperature such as 40°–150° C.), the nitro group was reduced an ring closure was effected, forming a dihydroquinolinone of the formula

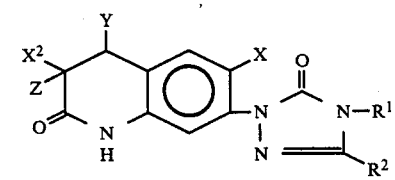

Formula V

The dihydroquinolinone was then dehydrohalogenated, as by treatment with a base such as triethylamine, to form a quinolinone of the formula Formula VI R[3] groups other than hydrogen may then be introduced by reaction with R[3]X[4] wherein X[4] is a leaving group such as halogen, e.g. Br or I.

As indicated above, the process involves the use of a reactant of the formula YHC=C(Z)—C(O)—X[3]. Among the reactants of this type which may be used are the following: methyl acrylate, ethyl acrylate, methyl methacrylate, methyl crotonate, methyl 3-chloroacrylate, methyl 2-methylene-4-pentenoate, and methyl 2-methylene-4-pentynoate.

To produce compounds in which R[3] is hydroxy or alkoxy the reduction and ring closure step may be effected by using a milder reducing agent (such as hydrazine in the presence of rhodium on carbon) to form, during the reaction, an intermediate having an —NHOH group (instead of an —NH$_2$ group) at the 5-position of the benzene ring so that on cyclization and dehydrohalogenation there is formed a compound having the formula Formula VII after which that compound may be treated with an appropriate alkylating agent in the presence of a base (e.g. methyl iodide in the presence of NaH).

Under some reaction conditions (illustrated in the Example below), the above-mentioned reactions starting with compound IV also result in the formation of a by-product which is a dihydroquinolinone of the formula Formula VIII which may be separated from the main product by, for instance, column chromatography. Dihydroquinolinones of formula VIII may also be produced by a catalytic hydrogenation (e.g. under basic conditions) of the above-illustrated quinolinones (e.g. of formula I or VI) and are also useful as herbicides. Another herbicidal by-product (which may be separated from the main product by, e.g. column chromatography) is a quinoline of the formula Formula IX Another procedure which may be employed instead of that shown in the Example involves similar steps but in a different order. Thus, one may start with a substituted aniline of the formula:

Formula X treat it according to the modified Meerwein reaction to form:

Formula XI nitrate the latter to form:

Formula XII subject XII to the reduction and ring closure to form;

Formula XIII and then subject XIII to the dehydrohalogenation to form:

Formula XIV followed by the reaction with R[3]X[4] to form:

Formula XV

This amine XV may then be converted to the corresponding triazolinone as by known reactions with sodium nitrite in hydrochloric acid followed by tin (IV) chloride pentahydrate and then pyruvic acid to form the hydrazone:

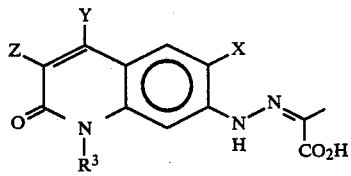

Formula XVI which is then reacted with, e.g., diphenylphosphoryl azide and triphenylamine in toluene to form:

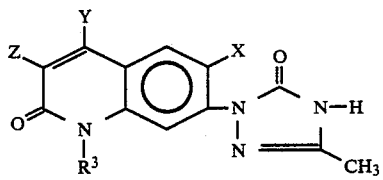

Formula XVII

Compound XVII is then reacted to introduce the $R^1$ substituent, as by reacting with chlorodifluoromethane and potassium hydroxide in tetrahydrofuran.

Representative compounds of this invention are tabulated below in Tables 1, 1A, and 1B. The following Example is given to illustrate this invention further. In this application all parts are by weight unless otherwise indicated.

EXAMPLE

Synthesis of 1-[6-fluoro-1-propylquinolin-2(1H)-one-7-yl]-4-difluoromethyl-4,5-dihydro-3-methyl-1,2,4-triazol-5(1H)-one

Step A

Synthesis of 2-fluoro-4-nitrophenylhydrazine

A solution of 3.2 g (0.10 mole) of hydrazine in 20 mL of isopropanol was added with stirring to a solution of 15.9 g (0.10 mole) of 3,4-difluoronitrobenzene in 60 mL of isopropanol. Upon completion of addition the reaction mixture was heated under reflux for 30 minutes. The reaction mixture was concentrated under reduced pressure to yield 15.5 g of 2-fluoro-4-nitrophenylhydrazine; m.p. 119°–121° C.

Step B

Synthesis of pyruvic acid, (2-fluoro-4-nitrophenyl)hydrazone

A solution of 15.0 g (0.09 mole) of 2-fluoro-4 nitrophenylhydrazine in 60 mL of ethanol was stirred and 8.8 g (0.1 mole) of pyruvic acid in 20 mL of water was added. Upon completion of addition the reaction mixture was stirred for an additional 30 minutes then filtered. The filter cake was washed with water and dried to yield 14.4 g o pyruvic acid, (2-fluoro-4-nitrophenyl)-hydrazone; m.p. 202°–203° C. The reaction was repeated.

Step C

Synthesis of 1-(2-fluoro-4-nitrophenyl)-4,5-dihydro-3-methyl-1,2,4-triazol-5(1H)-one A solution of 20.0 g (0.083 mole) of pyruvic acid, (2-fluoro-4-nitrophenyl)hydrazone in 100 mL of toluene was stirred and 8.4 g (0.083 mole) of triethylamine was added followed by 22.8 g (0.083 mole) of diphenylphosphoryl azide. Upon completion of addition the reaction mixture was slowly warmed to reflux temperature where it was stirred for 3 hours. The reaction mixture was then cooled to ambient temperature and was extracted with 100 mL of aqueous 10% sodium hydroxide solution. The extract was neutralized with concentrated hydrochloric acid. The resultant solid was collected by filtration and dried to yield 18.5 g of 1-(2-fluoro-4-nitrophenyl)-4,5-dihydro-3-methyl-1,2,4-triazol-5(1H)-one; m.p. 216°–217° C. The reaction was repeated.

Step D

Synthesis of 1-(2-fluoro-4-nitrophenyl)-4-difluoromethyl-4,5-dihydro-3-methyl-1,2,4-triazol-5(1H)-one To a suspension of 32.0 g (0.13 mole) of 1-(2- fluoro-4-nitrophenyl)-4,5-dihydro-3-methyl-1,2,4-triazol-5(1H)-one in 250 mL of tetrahydrofuran was added with stirring 17.7 g (0.30 mole) of crushed potassium hydroxide, followed by 1.0 g of terabutylammonium bromide and 60 mL of methylene chloride. The theoretical amount of chlorodifluoromethane was bubbled into the reaction mixture. Upon completion of addition the reaction mixture was stirred for an additional 30 minutes and then was cooled to ambient temperature. Water was added and the mixture was neutralized with concentrated hydrochloric acid. The resultant solid was extracted with ethyl acetate. The extract was dried with magnesium sulfate and filtered. The filtrate was concentrated under reduced pressure to a solid residue. The residue was stirred with methylene chloride, and insoluble starting material was collected by filtration. The filtrate was stirred under reflux for 18 hours in the presence of 100 mL of glacial acetic acid and 5 mL of concentrated hydrochloric acid. The mixture was then extracted with diethyl ether, and the extract was dried with magnesium sulfate. The mixture was filtered and the filtrate was concentrated under reduced pressure to yield 12.5 g of 1-(1-fluoro-4-nitrophenyl-4-difluoromethyl-4,5-dihydro-3-methyl-1,2,4-triazol-5(1H)-one; m.p. 82°–83° C. The nmr spectrum was consistent with the proposed structure.

Step E

Synthesis of 1-(4-amino-2-fluorophenyl)-4-difluoromethyl-4,5-dihydro-3-methyl-1,2,4-triazol-5(1H)-one A suspension of 10.5 g (0.036 mole) of 1-)2-fluoro-4-nitrophenyl)-4-difluoromethyl-4,5-dihydro-3-methyl -1,2,4-triazol-5(1H)-one and 0.3 g of platinum oxide in 200 mL of ethanol was hydrogenated using a parr hydrogenator. After one hour the theoretical amount of hydrogen had been consumed. The reaction mixture was filtered, and the filtrate concentrated under reduced pressure to give a residual oil. The oil was dissolved in methylene chloride, and the solution was filtered through a pad of silica gel. The filtrate was concentrated under reduced pressure to yield 9.0 g of 1-0(4-amino-2-fluorophenyl)-4-difluoromethyl-4,5-dihydro-3-methyl-1,2,4-triazol-5(1H)-one as an oil. The nmr spectrum was consistent with the proposed structure.

Step F

Synthesis of methyl 3-[3-fluoro-4-(4-difluoromethyl-4,5-dihydro-3-methyl-5-oxo-1H-1,2,4-triazol-1-yl)phenyl]-2-bromopropionate A mixture of 9.0 g (0.035 mole) of 1-(4-amino-2-fluorophenyl)-4-difluoromethyl-4,5-dihydro-3-methyl-1,2,4-triazol-5(1H)-one in 25 mL of 48% hydrobromide acid was stirred and 70 mL of acetone was added. The reaction mixture was cooled to 8° C. and a solution of 2.5 g (0.036 mole) of sodium nitrite in 7 mL of water was added below the surface of the reaction mixture. The reaction mixture temperature was kept below 15° C. during the addition. Upon completion of addition 25.0 g (0.30 mole) of methyl acrylate was added. The reaction mixture was then cooled to 0°–5° C. and 0.15 g of cuprous bromide was added slowly. Upon completion of addition the reaction mixture was allowed to warm to ambient temperature where it was stirred for 1 hour. After this time the reaction mixture was diluted with water and was extracted with diethyl ether. The ether extract was dried with magnesium sulfate and filtered. The filtrate was passed through a pad of silica gel and concentrated under reduced pressure to yield 11.3 g of methyl 3-[3-fluoro-4(4-difluoromethyl-4,5-dihydro-3-methyl-5-oxo-1H-1,2,4-triazol-1-yl)phenyl]-2-bromopropionate as an oil. The nmr spectrum was consistent with the proposed structure.

Step G

Synthesis of methyl 3-[5-fluoro-4-(4-difluoromethyl-4,5-dihydro-3-methyl-5-oxo-1H-1,2,4-triazol-1 -yl)-2-nitrophenyl]-2-bromopropionate A solution of 11.0 g 0.027 mole) of methyl 3-[3-fluoro-4-(4-difluoromethyl-4,5-dihydro-3-methyl-5-oxo-1H-1,2,4-triazol-1-yl)phenyl)-2-bromopropionate in 60 mL of concentrated sulfuric acid was stirred and cooled to 10°–15° C. To this was added 2.4 g (0.027 mole) of concentrated nitric acid. The reaction mixture temperature was maintained below 15° C. throughout the addition. Upon completion of addition the reaction mixture was allowed to warm to ambient temperature where it was stirred for 2 hours. The reaction mixture was poured slowly onto ice and the resultant solid was collected by filtration. The solid was dissolved in ethyl acetate and was passed through a pad of silica gel. The filtrate was concentrated under reduced pressure to yield 9.5 g of methyl 3-[5-fluoro-4-(4-difluoromethyl-4,5-dihydro-3-methyl-5-oxo-1H-1,2,4-triazol-1-yl)-2-nitrophenyl[-2-bromopropionate as an oil. The nmr spectrum was consistent with the proposed structure.

Step H

Synthesis of 1-(3-bromo-6-fluoro-3,4-dihydroquinolin-2(1H)-one-7-yl)-4-difluoromethyl-4,5-dihydro-3-methyl-1,2,4-triazol-5(1H)-one A solution of 9.0 g (0.020 mole) of methyl 3-[5- fluoro-4-(4-difluoromethyl-4,5-dihydro-3-methyl-5-oxo-1H-1,2,4-triazol-1-yl)-2-nitrophenyl]-2-bromopropionate in 100 mL of glacial acetic acid was stirred, and 9.0 mL of water was added. The reaction mixture was warmed to 40° C., and 9.0 g (0.16 mole) of iron powder was slowly added. Upon completion of addition the reaction mixture was allowed to cool to ambient temperature where it was stirred for 2 hours. The reaction mixture was filtered through a pad of diatomaceous earth. The filtrate was diluted with water, and the mixture was extracted with 100 mL of ethyl acetate. The filtrate was concentrated under reduced pressure to yield 7.5 g of 1-(3-bromo-6-fluoro-3,4-dihydroquinolin-2(1H)-one-7-yl)-4-difluoromethyl-4,5-dihydro-3-methyl-1,2,4-triazol-5(1H)-one as an oil. The nmr spectrum was consistent with the proposed structure.

Step I

Synthesis of 1-[6-fluoroquinolin-2(1H)-one-7-yl]-4-difluoromethyl-4,5-dihydro-3-methyl-1,2,4-triazol-5(1H)-one A solution of 7.0 g (0.018 mole) of 1-[3-bromo-6-fluoro-3,4-dihydroquinolin-2(1H)-one-7-yl)-4-difluoromethyl-4,5-dihydro-3-methyl-1,2,4-triazol-5(1H)-one in 60 mL of tetrahydrofuran was stirred, and 4.0 g (0.040 mole) of triethylamine was added. Upon completion of addition the reaction mixture was stirred at ambient temperature for 18 hours. The reaction mixture was concentrated under reduced pressure to give a residual solid. The solid was slurried in water and collected by filtration. The dried solid was slurried in 100 mL of hot ethyl acetate. The mixture was cooled, and the solid was collected by filtration to yield 3.6 g of 1-[6-fluoroquinolin-2(1H)-one-7-yl]-4-difluoromethyl-4,5-dihydro-3-methyl-1,2,4-triazol-5(1H)-one; m.p. 215°–217° C. The nmr spectrum was consistent with the proposed structure.

Step J

Synthesis of 1-[6-fluoro-1-propylquinolin-2(1H)-one-7-yl]-4-difluoromethyl-4,5-dihydro-3-methyl-1,2,4-triazol-5(1H)-one A suspension of 0.15 g (0.0032 mole) of sodium hydride in 30 mL of dimethylformamide was stirred, and 1.0 g (0.0032 mole) of 1-[6-fluoroquinolin-2(1H)-one-7-yl]-4-difluoromethyl-4,5-dihydro-3-methyl-1,2,4-triazol-5(1H)-one, followed by 1.0 g (0.0064 mole) of 1-iodopropane were added. The reaction mixture was stirred at ambient temperature for 18 hours, then was poured into water. The mixture was extracted with diethyl ether. The extract was dried with magnesium sulfate and filtered. The filtrate was concentrated under reduced pressure to a residue. The residue was subjected to column chromatography on silica gel. Elution was accomplished using 9:1 —methylene chloride: acetone. The appropriate fractions were combined and concentrated under reduced pressure to yield 0.1 g of 1-[6-fluoro-1-propylquinolin-2(1H)-one-7-yl]-4-difluoromethyl-45,-dihydro-3-methyl-1,2,4-triazol-5(1H)-one, m.p. 124°–125° C.

Analysis calculated for $C_{16}H_{15}F_3N_4O_2$: C 54.54, H 4.28, N 15.90; Found: C 54 65, H 3.91, N 15.92

The nmr spectrum was consistent with the proposed structure:

NMR (CDCl$_3$) d: 1.05(triplet, 3H of CH$_3$, J=8 Hz), 2.78(quartet, 2H of CH$_2$, J=8 Hz), 2.50 (singlet, 3H of CH$_3$), 4.25(triplet, 2H of CH$_2$, J=8 Hz), 6.77(doublet, 1H of vinyl H, J=10 Hz), 7.10(triplet, 1H of CF$_2$H, J=58 Hz), 7.42(doublet, 1H of ArH, J=10 Hz), 7.52(doublet, 1H of ArH, J=6 Hz), 7.62(doublet, 1H of vinyl H, J=10 Hz).

The column chromatography employed in Step J above also yielded some of each of compounds 2A and 2B of Tables 1A and 1B below.

Other compounds prepared in the manner above are:
1-[1-ethyl-6-fluoro-quinolin-2(1H)-one-7-yl]-4-difluoromethyl-4,5-dihydro-3-methyl-1,2,4-triazol-5(1H)-one; m.p. 176°–177° C.

The nmr spectrum was consistent with the proposed structure.

NMR (CDCl$_3$) d: 1.37(triplet, 3H of CH$_3$, J=8 Hz), 2.52(singlet, 3H of CH$_3$), 4.36(quartet, 4H of CH$_2$, J=7 Hz), 6.77(doublet, 1H of vinyl H, J=10 Hz), 7.09(triplet, 1H of CF$_2$H, J=58 Hz), 7.42(doublet, 1H of ArH, J=10 Hz), 7.52(doublet, 1H of ARH, J=6 Hz), 7.62(doublet, 1H of vinyl H, J=10 Hz).

1-[6-fluoro-1-(2-propenyl)-quinolin-2(1H)-one-7-yl]-4-difluoromethyl-4,5-dihydro-3-methyl-1,2,4-triazol-5(1H)-one; m.p. 146°–147° C.

The nmr spectrum was consistent with the proposed structure:

NMR (CDCl$_2$) d: 2.50(singlet, 3H of CH$_3$), 4.92(doublet, 2H of N-CH$_2$, J=3 Hz), 5.10(doublet, 1H of vinyl H, J=17 Hz), 5.25(doublet, 1H of vinyl H, J=11 Hz), 5.92(multiplet, 1H of vinyl H), 6.89(doublet, 1H of vinyl H, J=10 Hz), 7.08(triplet, 1H of CF$_2$H, J=58 Hz), 7.40(doublet, 1H of ArH, J=10 Hz), 7.49(doublet, 1H of ArH, J=6 Hz), 7.64(doublet, 1H of vinyl H, J=10 Hz).

HERBICIDAL ACTIVITY

The plant test species used in demonstrating the herbicidal activity of compounds of this invention include cotton (*Gossypoium hirsutum* var. Stoneville), soybean (*Glycine max* var. Williams), field corn (*Zea mays* var. Agway 595S), wheat (*Triticum aestivium* var. Prodax), rice (*Oryza sativa*), morningglory (*Ipomea lacumosa* or *Ipomea hederacea*), wild mustard (*Brassica kaber*), velvetleaf (*Abutilon theoohrasti*), barnyardgrass (*Echinochloa crus-galli*), green foxtail (*Setaria viridis*), and johnsongrass (*Sorghum halepense*).

Preparation of Flats

Preemergence:

Two disposable fiber flats (8 cm×15 cm×25 cm) for each rate of application for each candidate herbicide are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below. Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Alabama, 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight | Some dis- | Poor weed |

Herbicide Rating System (continued)

| Rating Percent Control | Description of Main Categories | Crop Description | Weed Description |
|---|---|---|---|
| | effect | coloration, stunting or stand loss | control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Tables 3 and 4 below. The test compounds are identified by numbers which correspond to those used in Tables 1, 1A, and 1B.

In the tables of herbicidal data below, "kg/ha" is kilograms per hectare.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkylnaphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate | |

| Component: | % by Wt. |
|---|---|
| and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively nonvolatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, compound 7 of the tables below has, in greenhouse testing at pre-emergence dosages as low as about 0.015 kg/ha, given good weed control with no damage to cotton. For field use, where there are losses of herbicide, larger dosages (e.g. four times the dosage mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

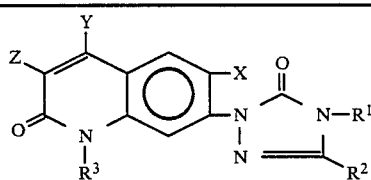

| Cmpd. No. | $R^1$ | $R^2$ | X | Y | Z | $R^3$ |
|---|---|---|---|---|---|---|
| 1 | $CH_3$ | $CH_3$ | F | H | H | n-$C_3H_7$ |
| 2 | $C_2H_5$ | $CH_3$ | F | H | H | n-$C_3H_7$ |
| 3 | n-$C_3H_7$ | $CH_3$ | F | H | H | n-$C_3H_7$ |
| 4 | $CH(CH_3)_2$ | $CH_3$ | F | H | H | n-$C_3H_7$ |
| 5 | $CHF_2$ | $CH_3$ | F | H | H | $CH_3$ |
| 6 | $CHF_2$ | $CH_3$ | F | H | H | $C_2H_5$ |
| 7 | $CHF_2$ | $CH_3$ | F | H | H | n-$C_3H_7$ |
| 8 | $CHF_2$ | $CH_3$ | F | H | H | $CH(CH_3)_2$ |
| 9 | $CHF_2$ | $CH_3$ | F | H | H | n-$C_4H_9$ |
| 10 | $CHF_2$ | $CH_3$ | F | H | H | $(CH_2)_2CH(CH_3)_2$ |
| 11 | $CHF_2$ | $CH_3$ | F | H | H | $CH_2CH_2F$ |
| 12 | $CHF_2$ | $CH_3$ | F | H | H | $CH_2CH_2CH_2F$ |
| 13 | $CHF_2$ | $CH_3$ | F | H | H | $CHF_2$ |
| 14 | $CHF_2$ | $CH_3$ | F | H | H | $OCH_3$ |
| 15 | $CHF_2$ | $CH_3$ | F | H | H | $CH_2OCH_3$ |
| 16 | $CHF_2$ | $CH_3$ | F | H | H | $CH_2CH_2OCH_3$ |
| 17 | $CHF_2$ | $CH_3$ | F | H | H | $CH_2CN$ |
| 18 | $CHF_2$ | $CH_3$ | F | H | H | $CH_2CH=CH_2$ |
| 19 | $CHF_2$ | $CH_3$ | F | H | H | $CH_2CCl=CH_2$ |
| 20 | $CHF_2$ | $CH_3$ | F | H | H | $CH_2CH=CCl_2$ |
| 21 | $CHF_2$ | $CH_3$ | F | H | H | $CH_2C\equiv CH$ |
| 22 | $CHF_2$ | $CH_3$ | F | H | H | $CH_2CO_2CH_3$ |
| 23 | $CHF_2$ | $CH_3$ | F | Cl | H | n-$C_3H_7$ |
| 24 | $CHF_2$ | $CH_3$ | F | Br | H | n-$C_3H_7$ |
| 25 | $CHF_2$ | $CH_3$ | F | $CH_3$ | H | n-$C_3H_7$ |
| 26 | $CHF_2$ | $CH_3$ | F | $CHF_2$ | H | n-$C_3H_7$ |
| 27 | $CHF_2$ | $CH_3$ | F | $NO_2$ | H | n-$C_3H_7$ |
| 28 | $CHF_2$ | $CH_3$ | F | H | Cl | n-$C_3H_7$ |
| 29 | $CHF_2$ | $CH_3$ | F | H | Br | n-$C_3H_7$ |
| 30 | $CHF_2$ | $CH_3$ | F | H | F | n-$C_3H_7$ |
| 31 | $CHF_2$ | $CH_3$ | F | H | $CH_3$ | n-$C_3H_7$ |
| 32 | $CHF_2$ | $CH_3$ | F | H | $CH(CH_3)_2$ | n-$C_3H_7$ |
| 33 | $CHF_2$ | $CH_3$ | F | H | $CHF_2$ | n-$C_3H_7$ |
| 34 | $CHF_2$ | $CH_3$ | F | H | $CF_3$ | n-$C_3H_7$ |
| 35 | $CHF_2$ | $CH_3$ | F | H | $OCH_3$ | n-$C_3H_7$ |
| 36 | $CHF_2$ | $CH_3$ | F | H | $OCHF_2$ | n-$C_3H_7$ |
| 37 | $CHF_2$ | $CH_3$ | F | H | $SCH_3$ | n-$C_3H_7$ |
| 38 | $CHF_2$ | $CH_3$ | F | H | $SO_2CH_3$ | n-$C_3H_7$ |
| 40 | $CHF_2$ | $CH_3$ | F | H | $NO_2$ | n-$C_3H_7$ |
| 41 | $CHF_2$ | $CH_2CH_3$ | F | H | H | n-$C_3H_7$ |
| 42 | $CHF_2$ | $CH(CH_3)_2$ | F | H | H | n-$C_3H_7$ |
| 43 | $CHF_2$ | $CHF_2$ | F | H | H | n-$C_3H_7$ |
| 44 | $CHF_2$ | $OCH_3$ | F | H | H | n-$C_3H_7$ |
| 45 | $CHF_2$ | $OCH(CH_3)_2$ | F | H | H | n-$C_3H_7$ |
| 46 | $CHF_2$ | $OCHF_2$ | H | H | H | n-$C_3H_7$ |
| 47 | $CHF_2$ | $OCHF_2$ | Cl | H | H | n-$C_3H_7$ |
| 48 | $CHF_2$ | $OCHF_2$ | Br | H | H | n-$C_3H_7$ |
| 49 | $CHF_2$ | $OCHF_2$ | F | H | H | n-$C_3H_7$ |
| 50 | $CHF_2$ | $OCHF_2$ | $CH_3$ | H | H | n-$C_3H_7$ |
| 51 | $CHF_2$ | $OCHF_2$ | $CHF_2$ | H | H | n-$C_3H_7$ |
| 52 | $CHF_2$ | $OCHF_2$ | $CF_3$ | H | H | n-$C_3H_7$ |
| 53 | $CHF_2$ | $SCH_3$ | F | H | H | n-$C_3H_7$ |
| 54 | $CHF_2$ | $SO_2CH_3$ | F | H | H | n-$C_3H_7$ |
| 55 | $CH_2CH_2F$ | $CH_3$ | F | H | H | n-$C_3H_7$ |
| 56 | $CH_2CH_2CH_2F$ | $CH_3$ | F | H | H | n-$C_3H_7$ |
| 57 | $CH_2OCH_3$ | $CH_3$ | F | H | H | n-$C_3H_7$ |
| 58 | $CH_2CH=CH_2$ | $CH_3$ | F | H | H | n-$C_3H_7$ |
| 59 | $CH_2C\equiv CH$ | $CH_3$ | F | H | H | n-$C_3H_7$ |
| 60 | $CHF_2$ | $CH_3$ | Cl | H | H | $CH(CH_3)_2$ |
| 61 | $CHF_2$ | $CH_3$ | Cl | H | H | $CH_2CH_2CH_3$ |
| 62 | $CHF_2$ | $CH_3$ | Cl | H | H | $CH_2CH=CH_2$ |
| 63 | $CHF_2$ | $CH_3$ | Cl | H | H | $CH_2C\equiv CH$ |
| 64 | $CHF_2$ | $CH_3$ | Cl | H | $CH_3$ | $CH_2C\equiv CH$ |
| 65 | $CHF_2$ | $CH_3$ | Cl | H | Cl | $CH_2C\equiv CH$ |
| 66 | $CHF_2$ | $CH_3$ | Cl | H | H | $CH_2OCH_3$ |

TABLE 1-continued

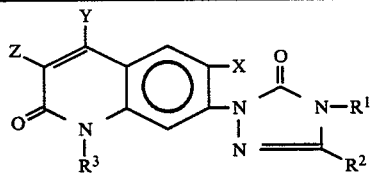

| Cmpd. No. | R¹ | R² | X | Y | Z | R³ |
|---|---|---|---|---|---|---|
| 67 | CHF$_2$ | CH$_3$ | F | H | H | H |
| 68 | CHF$_2$ | CH$_3$ | F | H | CH$_3$ | H |
| 69 | CHF$_2$ | CH$_3$ | F | H | CH$_3$ | CH$_2$CH=CH$_2$ |
| 70 | CHF$_2$ | CH$_3$ | F | H | CH$_3$ | CH$_2$C≡CH |
| 71 | CHF$_2$ | CH$_3$ | F | H | H | CH$_2$CH$_2$CH$_2$Cl |
| 72 | CHF$_2$ | CH$_3$ | F | H | H | CH$_2$OCH$_2$OC$_2$H$_5$ |
| 73 | CHF$_2$ | CH$_3$ | F | H | H | CH(CH$_2$)$_4$CH$_2$ |
| 74 | CHF$_2$ | CH$_3$ | F | H | H | CH$_2$CHCH$_2$CH$_2$ |
| 75 | CHF$_2$ | CH$_3$ | F | H | H | CH$_2$SCH$_3$ |
| 76 | CHF$_2$ | CH$_3$ | F | H | H | CH$_2$C$_6$H$_5$ |
| 77 | CHF$_2$ | CH$_3$ | F | H | H | OH |
| 78 | CHF$_2$ | CH$_3$ | F | F | H | n-C$_3$H$_7$ |
| 79 | CHF$_2$ | CH$_3$ | F | CO$_2$CH$_3$ | H | n-C$_3$H$_7$ |
| 80 | CHF$_2$ | CH$_3$ | F | CN | H | n-C$_3$H$_7$ |
| 81 | CHF$_2$ | CH$_3$ | F | H | CH$_2$CH=CH$_2$ | n-C$_3$H$_7$ |
| 82 | CHF$_2$ | CH$_3$ | F | H | CH$_2$C≡CH | n-C$_3$H$_7$ |
| 83 | CHF$_2$ | CH$_3$ | F | H | S(O)CH$_3$ | n-C$_3$H$_7$ |
| 84 | CH$_2$OCHF$_2$ | CH$_3$ | F | H | H | n-C$_3$H$_7$ |
| 85 | CHF$_2$ | S(O)CH$_3$ | F | H | H | n-C$_3$H$_7$ |
| 86 | CHF$_2$ | F | F | H | H | n-C$_3$H$_7$ |
| 87 | CHF$_2$ | Cl | F | H | H | n-C$_3$H$_7$ |
| 88 | CHF$_2$ | Br | F | H | H | n-C$_3$H$_7$ |

TABLE 1A

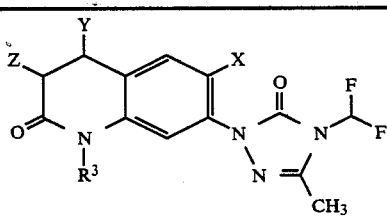

| Cmpd No. | X | Y | Z | R³ |
|---|---|---|---|---|
| 1A | F | H | H | H |
| 2A | F | H | H | CH$_2$CH$_2$CH$_3$ |
| 3A | F | H | Cl | H |
| 4A* | F | H | Cl,CH$_3$ | H |
| 5A | F | Cl | Cl | H |

*The H atom on the carbon atom bearing the Z substituent has been replaced with a second Z substituent.

TABLE 1B

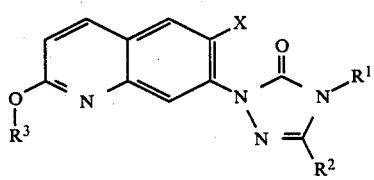

| Cmpd. No. | X | R¹ | R² | R³ |
|---|---|---|---|---|
| 1B | F | CHF$_2$ | CH$_3$ | CH$_2$CH$_3$ |
| 2B | F | CHF$_2$ | CH$_3$ | CH$_2$CH$_2$CH$_3$ |
| 3B | F | CHF$_2$ | CH$_3$ | CH$_2$CH=CH$_2$ |

TABLE 1B-continued

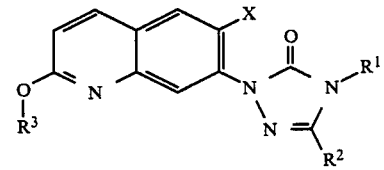

| Cmpd. No. | X | R¹ | R² | R³ |
|---|---|---|---|---|
| 4B | F | CHF$_2$ | CH$_3$ | CH$_2$C≡CH |

TABLE 2

| Cmpd No. | MP (°C.) | Emperical Formula | Elemental Analysis | | |
|---|---|---|---|---|---|
| | | | C | H | N |
| 6 | 176–177 | C$_{15}$H$_{13}$F$_3$N$_4$O$_2$ | C 54.54 | 4.28 | 15.90 |
| 7 | 124–125 | C$_{16}$H$_{15}$F$_3$N$_4$O$_2$ | F 54.65 | 3.91 | 15.92 |
| 18 | 146–147 | C$_{16}$H$_{13}$F$_3$N$_4$O$_2$ | C 54.86 | 3.73 | 15.99 |
| | | | F 55.55 | 3.74 | 15.55 |
| 21 | 187–188 | C$_{16}$H$_{11}$F$_3$N$_4$O$_2$ | C 55.17 | 3.18 | 16.08 |
| | | | F 55.30 | 2.93 | 15.18 |
| 67 | 215–217 | C$_{13}$H$_9$F$_3$N$_4$O$_2$ | C 56.35 | 3.61 | 15.46 |
| 68 | 269–270 | C$_{14}$H$_{11}$F$_3$N$_4$O$_2$ | F 56.19 | 3.60 | 15.23 |
| 69 | 145–147 | C$_{17}$H$_{15}$F$_3$N$_4$O$_2$ | | | |
| 70 | 186–188 | C$_{17}$H$_{13}$F$_3$N$_4$O$_2$ | | | |
| 1A | oil | C$_{13}$H$_{10}$BrF$_3$N$_4$O$_2$ | C 54.23 | 4.79 | 15.81 |
| 2A | 139–140 | C$_{16}$H$_{17}$F$_3$N$_4$O$_2$ | F 54.19 | 4.64 | 15.37 |
| 3A | 201–202 | C$_{13}$H$_{10}$ClF$_3$N$_4$O$_2$ | | | |
| 4A | oil | C$_{14}$H$_{12}$ClF$_3$N$_4$O$_2$ | | | |
| 5A | 122–123 | C$_{13}$H$_{19}$Cl$_2$F$_3$N$_4$O$_2$ | | | |
| 1B | 138–139 | C$_{15}$H$_{13}$F$_3$N$_4$O$_2$ | C 54.54 | 4.28 | 15.90 |
| 2B | 89–90 | C$_{16}$H$_{15}$F$_3$N$_4$O$_2$ | F 55.92 | 4.54 | 15.43 |
| 3B | 107–108 | C$_{16}$H$_{13}$F$_3$N$_4$O$_2$ | | | |

TABLE 2-continued

| Cmpd No. | MP (°C.) | Emperical Formula | Elemental Analysis C | H | N |
|---|---|---|---|---|---|
| 4B | 188–189 | $C_{16}H_{11}F_3N_4O_2$ | | | |

TABLE 3
PREEMERGENCE HERBICIDAL ACTIVITY
% Control

| Compound No. | 6 | 7 | 18 | 21 |
|---|---|---|---|---|
| Rate (kg/ha) | 0.25 | 0.25 | 0.25 | 0.125 |
| Species | | | | |
| Cotton | 80 | 5 | 90 | 70 |
| Soybean | 100 | 40 | 100 | 95 |
| Field Corn | 100 | 95 | 95 | 100 |
| Rice | 100 | 70 | 100 | 95 |
| Wheat | 100 | 60 | 100 | 95 |
| Morningglory | 100 | 100 | 100 | 100 |
| Wild Mustard | 100 | 100 | 100 | 100 |
| Velvetleaf | 100 | 100 | 100 | 100 |
| Barnyardgrass | 100 | 100 | 100 | 100 |
| Green Foxtail | 100 | 100 | 100 | 100 |
| Johnsongrass | 100 | 100 | 100 | 100 |
| Compound No. | 67 | 68 | 69 | 70 |
| Rate (kg/ha) | 8.0 | 2.0 | 0.25 | 0.125 |
| Species | | | | |
| Cotton | — | 90 | 95 | 80 |
| Soybean | 95 | 90 | 95 | 100 |
| Field Corn | 90 | 100 | 100 | 100 |
| Rice | — | 60 | 70 | 70 |
| Wheat | 90 | 70 | 70 | 40 |
| Morningglory | 90 | 100 | 100 | 100 |
| Wild Mustard | — | 100 | 100 | 100 |
| Velvetleaf | 100 | 100 | 100 | 100 |
| Barnyardgrass | 90 | 95 | 100 | 95 |
| Green Foxtail | 100 | 100 | 100 | 100 |
| Johnsongrass | — | 100 | 100 | 95 |
| Compound No. | 1A | 2A | 3A | 4A |
| Rate (kg/ha) | 8.0 | 0.25 | 1.0 | 2.0 |
| Species | | | | |
| Cotton | — | 5 | 10 | 50 |
| Soybean | 100 | 70 | 10 | 70 |
| Field Corn | 90 | 95 | 20 | 95 |
| Rice | — | 80 | 30 | 40 |
| Wheat | 95 | 80 | 40 | 30 |
| Morningglory | 100 | 95 | 70 | 70 |
| Wild Mustard | — | 100 | — | 20 |
| Velvetleaf | 100 | 80 | 95 | 100 |
| Barnyardgrass | 100 | 95 | 60 | 60 |
| Green Foxtail | 100 | 100 | 40 | 90 |
| Johnsongrass | — | 90 | 20 | 80 |
| Compound No. | 5A | 1B | 2B | 3B | 4B |
| Rate (kg/ha) | 1.0 | 0.25 | 0.25 | 0.25 | 0.5 |
| Species | | | | | |
| Cotton | 5 | 0 | 0 | 0 | 0 |
| Soybean | 20 | 0 | 0 | 0 | 5 |
| Field Corn | 5 | 0 | 0 | 0 | 0 |
| Rice | 20 | 0 | 5 | 20 | 0 |
| Wheat | — | 0 | 0 | 20 | 10 |
| Morningglory | 40 | 50 | 50 | 20 | 0 |
| Wild Mustard | — | 0 | 0 | 10 | 5 |
| Velvetleaf | 95 | 40 | 20 | 60 | 20 |
| Barnyardgrass | 50 | 80 | 60 | 90 | 0 |
| Green Foxtail | 90 | 100 | 95 | 100 | 5 |
| Johnsongrass | 60 | 100 | 95 | 90 | 50 |

TABLE 4
POSTEMERGENCE HERBICIDAL ACTIVITY
% Control

| Compound No. | 6 | 7 | 18 | 21 |
|---|---|---|---|---|
| Rate (kg/ha) | 0.25 | 0.25 | 0.25 | 0.125 |
| Species | | | | |
| Cotton | 100 | 90 | 100 | 100 |
| Soybean | 100 | 80 | 100 | 100 |
| Field Corn | 100 | 80 | 100 | 100 |
| Rice | 95 | 80 | 100 | 95 |
| Wheat | 100 | 80 | 95 | 100 |
| Morningglory | 100 | 100 | 100 | 100 |
| Wild Mustard | 100 | 100 | 100 | 100 |
| Velvetleaf | 100 | 100 | 100 | 100 |
| Barnyardgrass | 100 | 100 | 100 | 100 |
| Green Foxtail | 100 | 100 | 100 | 100 |
| Johnsongrass | 100 | 100 | 100 | 100 |
| Compound No. | 67 | 68 | 69 | 70 |
| Rate (kg/ha) | 8.0 | 2.0 | 0.25 | 0.125 |
| Species | | | | |
| Cotton | — | 90 | 100 | 100 |
| Soybean | 95 | 90 | 90 | 100 |
| Field Corn | 95 | 90 | 70 | 100 |
| Rice | — | 60 | 50 | 80 |
| Wheat | 90 | 50 | 100 | 100 |
| Morningglory | 100 | 100 | 100 | 100 |
| Wild Mustard | — | 100 | 100 | 100 |
| Velvetleaf | 100 | 100 | 100 | 100 |
| Barnyardgrass | 95 | 100 | 100 | 100 |
| Green Foxtail | 100 | 100 | 100 | 100 |
| Johnsongrass | — | 85 | 100 | 100 |
| Compound No. | 1A | 2A | 3A | 4A |
| Rate (kg/ha) | 8.0 | 0.25 | 1.0 | 2.0 |
| Species | | | | |
| Cotton | — | 70 | 90 | 95 |
| Soybean | 95 | 80 | 80 | 95 |
| Field Corn | 90 | 95 | 60 | 90 |
| Rice | — | 80 | 10 | 40 |
| Wheat | 80 | 70 | 20 | 30 |
| Morningglory | 100 | 100 | 100 | 100 |
| Wild Mustard | — | 100 | 70 | 85 |
| Velvetleaf | 100 | 100 | 100 | 100 |
| Barnyardgrass | 100 | 100 | 10 | 95 |
| Green Foxtail | 100 | 100 | 80 | 100 |
| Johnsongrass | — | 95 | 10 | 70 |
| Compound No. | 5A | 1B | 2B | 3B | 4B |
| Rate (kg/ha) | 1.0 | 0.25 | 0.25 | 0.25 | 0.5 |
| Species | | | | | |
| Cotton | 70 | 70 | 80 | 70 | 40 |
| Soybean | 90 | 60 | 40 | 50 | 40 |
| Field Corn | 50 | 50 | 40 | 40 | 30 |
| Rice | 10 | 10 | 10 | 10 | 10 |
| Wheat | 30 | 60 | 30 | 20 | 10 |
| Morningglory | 100 | 100 | 100 | 100 | 60 |
| Wild Mustard | 85 | 10 | 50 | 80 | 70 |
| Velvetleaf | 100 | 95 | 100 | 100 | 70 |
| Barnyardgrass | 100 | 60 | 60 | 95 | 10 |
| Green Foxtail | 80 | 40 | 70 | 80 | 90 |
| Johnsongrass | 70 | 40 | 70 | 80 | 10 |

I claim:
1. An herbicidal compound of the formula

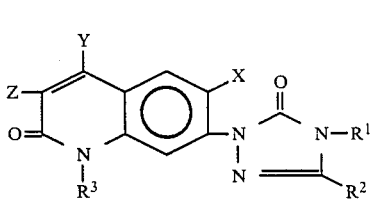

in which:
$R^3$ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy;
X is H, halogen, alkyl, or haloalkyl;

Y is H, halogen, alkyl, haloalkyl, alkoxycarbonyl, cyano, or nitro;

Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro;

R¹ is alkyl, alkenyl, alkynyl, haloalkyl, alkoxyalkyl, or haloalkoxyalkyl; and

R² is alkyl, haloalkyl, alkoxy, haloalkoxy, alkylthio, alkylsulfinyl, alkylsulfonyl, or halogen.

2. The herbicidal compound of claim 1 in which any alkyl, alkenyl, or alkynyl group or moiety has up to 6 carbon atoms and cycloalkyl has 3 to 7 ring carbon atoms.

3. The herbicidal compound of claim 2 in which aralkyl is benzyl.

4. The herbicidal compound of claim 3 in which any alkyl, alkenyl, or alkynyl group or moiety has up to 4 carbon atoms.

5. The compound of claim 4 in which R² is methyl.

6. The compound of claim 5 in which R¹ is haloalkyl.

7. The compound of claim 6 in which X is halogen.

8. The compound of claim 7 in which Y is H.

9. The compound of claim 8 in which Z is H or methyl.

10. The compound of claim 9 in which R³ is alkyl, allyl, methallyl, propynyl, methylpropynyl, 3-chloropropyl, 2-fluoroethyl, 3-fluoropropyl, 3,3-dichloro-2-propenyl, methoxymethyl, ethoxymethyl, ethoxymethoxymethyl, cyclopropylmethyl, methylthiomethyl, benzyl, cyanomethyl, alkoxycarbonylmethyl, hydroxy, methoxy, or ethoxy.

11. The compound of claim 10 in which R³ is alkyl.

12. The compound of claim 11 in which X is F and Z is H.

13. The compound of claim 12 in which R¹ is CHF₂.

14. The compound of claim 13 in which R³ is n-C₃H₇.

15. An herbicidal composition comprising an herbicidally effective amount of the compound of claim 1 in admixture with a suitable carrier.

16. A method for controlling undesired plant growth which comprises applying to the locus where control is desired an herbicidally effective amount of the composition of claim 15.

17. An herbicidal composition comprising an herbicidally effective amount of the compound of claim 2 in admixture with a suitable carrier.

18. A method for controlling undesired plant growth which comprises applying to the locus where control is desired an herbicidally effective amount of the composition of claim 17.

19. An herbicidal composition comprising an herbicidally effective amount of the compound of claim 3 in admixture with a suitable carrier.

20. A method for controlling undesired plant growth which comprises applying to the locus where control is desired an herbicidally effective amount of the composition of claim 19.

21. An herbicidal compound of the formula

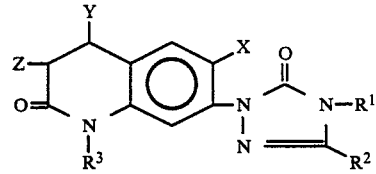

in which:

R³ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy;

X is H, halogen, alkyl, or haloalkyl;

Y is H, halogen, alkyl, haloalkyl, alkoxycarbonyl, cyano, or nitro;

Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro;

R¹ is alkyl, alkenyl, alkynyl, haloalkyl, alkoxyalkyl, or haloalkoxyalkyl; and

R² is alkyl, haloalkyl, alkoxy, haloalkoxy, alkylthio, alkylsulfinyl, alkylsulfonyl, or halogen;

and in which any alkyl, alkenyl, or alkynyl, group or moiety has up to 6 carbon atoms and cycloalkyl has 3 to 7 carbon atoms.

22. The compound of claim 21 in which any alkyl, alkenyl, or alkynyl group or moiety has up to 4 carbon atoms and aralkyl is benzyl.

23. The compound of claim 22 in which R¹ is CHF₂, R² is CH₃, X is F, Y is H or halogen, Z is H, halogen, or alkyl, and R³ is alkyl.

24. The compound of claim 23 in which Y is H and R³ is n-C₃H₇.

25. An herbicidal composition comprising an herbicidally effective amount of the compound of claim 21 in admixture with a suitable carrier.

26. A method for controlling undesired plant growth which comprises applying to the locus where control is desired an herbicidally effective amount of the composition of claim 25.

27. An herbicidal composition comprising an herbicidally effective amount of the compound of claim 22 in admixture with a suitable carrier.

28. A method for controlling undesired plant growth which comprises applying to the locus where control is desired an herbicidally effective amount of the composition of claim 27.

* * * * *